United States Patent [19]

Ishikawa

[11] Patent Number: 5,178,609
[45] Date of Patent: Jan. 12, 1993

[54] MEDICAL LIQUID INJECTOR FOR CONTINUOUS TRANSFUSION

[75] Inventor: Toichi Ishikawa, Yokohama, Japan

[73] Assignee: Kato Hatsujo Kaisha, Ltd., Yokohama, Japan

[21] Appl. No.: 710,636

[22] Filed: Jun. 5, 1991

[30] Foreign Application Priority Data

Jun. 19, 1990 [JP] Japan ................... 2-161066

[51] Int. Cl.⁵ ............... A61M 27/00; A61M 5/20
[52] U.S. Cl. ..................... 604/131; 604/135; 604/228; 128/DIG. 12
[58] Field of Search ............ 604/187, 130, 208, 218, 604/82, 83, 89, 228, 131, 132, 134, 135; 128/DIG. 12

[56] References Cited

U.S. PATENT DOCUMENTS

| | | | |
|---|---|---|---|
| 2,183,482 | 12/1939 | Kurkjian | 604/135 |
| 2,309,502 | 1/1943 | Douglas . | |
| 2,605,765 | 8/1952 | Kollsman | 604/135 |
| 3,214,067 | 10/1965 | Linington | 604/130 |
| 3,797,488 | 3/1974 | Hurschman et al. | 604/136 |
| 3,880,163 | 4/1975 | Ritterskamp . | |
| 4,022,207 | 5/1977 | Citrin | 604/218 X |
| 4,267,836 | 5/1981 | Whitney et al. | 604/135 |
| 4,547,189 | 10/1985 | Moore | 604/136 |
| 4,627,835 | 12/1986 | Fenton | 604/67 |
| 4,735,611 | 4/1988 | Anderson et al. . | |
| 4,849,032 | 7/1989 | Kawaguchi . | |
| 4,921,487 | 5/1990 | Buffet et al. | 604/135 |
| 4,991,742 | 2/1991 | Chang | 222/95 |
| 4,997,420 | 3/1991 | LaFevre | 604/121 |
| 5,100,389 | 3/1992 | Vaillancourt | 604/135 |

FOREIGN PATENT DOCUMENTS

| | | | |
|---|---|---|---|
| 0114145 | 7/1984 | European Pat. Off. . | |
| 0388102 | 9/1990 | European Pat. Off. | 604/187 |
| 3340511 | 2/1985 | Fed. Rep. of Germany | 604/187 |
| 3827525 | 2/1990 | Fed. Rep. of Germany | 604/187 |
| 2429599 | 2/1980 | France | 604/208 |

Primary Examiner—C. Fred Rosenbaum
Assistant Examiner—Mark O. Polutta
Attorney, Agent, or Firm—Nikaido, Marmelstein, Murray & Oram

[57] ABSTRACT

A medical liquid injector for continuous transfusion includes a syringe fitted with a piston having a detachable shaft rod, and a cap that can be connected to a proximal end portion of the syringe. The cap has an elastic pressing device for continuously pressing the piston from which the shaft rod is removed to a position where all the amount of medical liquid is pushed out after the medical liquid has been sucked into the syringe.

1 Claim, 4 Drawing Sheets

MEDICAL LIQUID INJECTOR FOR CONTINUOUS TRANSFUSION

BACKGROUND OF THE INVENTION

1. Field of the Invention

Present invention relates to a medical liquid injector for continuously transfusing a predetermined type of medical liquid into a human body (blood vessel or bladder) little by little.

2. Description of the Related Art

Conventional injectors of the above-described type include (1) a transfusion set for continuously transfusing a medical liquid into a human body little by little utilizing a head of the medical liquid contained in a transfusion bottle, and (2) an injector with a balloon for continuously injecting a medical liquid filled in a balloon made of rubber into a human body little by little utilizing the contracting force of the balloon.

However, the transfusion bottle of the transfusion set must be hung at a high position, and a patient must stay quite still while he or she is given a drip transfusion.

The injector with the balloon has an advantage in that it can be carried from one place to another easily, unlike the transfusion set. However, there is a limitation to the contracting force of the balloon, and the medical liquid contained in the balloon cannot be used up and hence wasted.

In view of the aforementioned drawbacks of the conventional injector, an object of the present invention is to provide an injector for continuously injecting a medical liquid which can be easily carried from one place to another, which is capable of continuous injection of the medical liquid at a fixed rate; and which enables the medical liquid contained in a cylinder to be used up to the last drop.

SUMMARY OF THE INVENTION

To achieve this object, the present invention provides in one aspect a medical liquid injector for continuous transfusion which comprises a syringe having a piston with a detachable shaft rod, and a cap that can be connected to a proximal end portion of the syringe. The cap has an elastic pressing device for continuously pressing the piston from which the shaft rod is removed, to a position where the full amount of medical liquid is pushed out after the medical liquid has been sucked into the syringe.

The present invention provides in another aspect a medical liquid injector for continuous transfusion which comprises a syringe having a piston with a detachable shaft rod, a casing for fixing the syringe, and a resilient pressing means set on a side wall of the casing facing a proximal end of the syringe, which after the medical liquid had been sucked out into the syringe, is capable of continuously pressing the piston from which the shaft rod has been detached, up to the position where the full amount of the medical liquid is pushed out. The resilient pressing means may be formed by utilizing a super resilient area of a shape memory alloy spring.

Other objects and advantages of the invention will become apparent from the following description of embodiments with reference to the accompanying drawings.

DETAILED DESCRIPTION OF THE PREFERRED EMBODIMENTS

Figure 1:
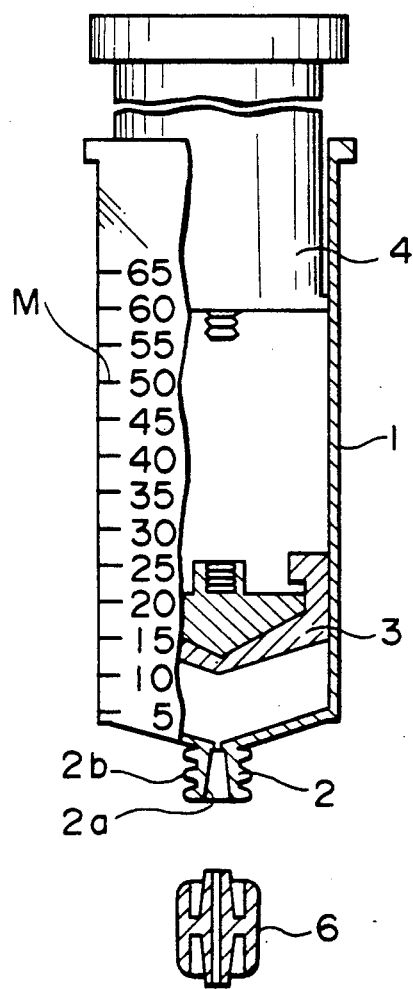
FIG. 1 is a cross-sectional view of a syringe and an injection needle used when a medical liquid is drawn in, showing a first embodiment of the present invention.
Figure 1:
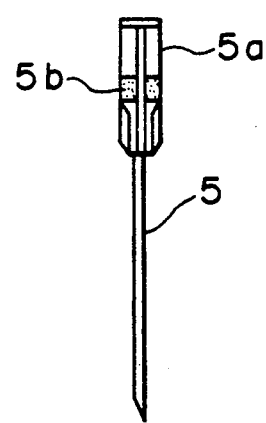

The present invention will now be described in detail with reference to the accompanying drawings.

A first embodiment of the present invention will be described first with reference to FIGS. 1 to 5. A syringe 1 of the injector according to the present invention is closed at one end thereof. The syringe 1 has a base 2 on the closed end thereof. The proximal end of the syringe 1 is open. The syringe 1 has a piston 3 fitted therein in such a manner that the piston 3 can slide along the inner wall thereof. The piston 3 has at the center of a rear surface thereof a boss into which the distal end of a shaft rod 4 can be screwed. That is, the shaft rod 4 can be removed from the piston 3 after the medical liquid has been drawn in the syringe 1 which is achieved by pulling the piston 3. The inner surface of the base 2 is tapered in such a manner that the inner diameter increases toward the end thereof to form a tapered surface 2a. The outer surface of the base 2 is externally threaded to form a male screw (annular rib) 2b.

A needle 5 can be connected to the base 2 of the syringe 1 with a first connection piece 6 therebetween. The needle 5 is used to draw the medical liquid into the syringe 1. A filter 5b is provided at a proximal end 5a of the needle 5 to prevent impurities from flowing into the syringe 1 together with the medical liquid.

The quantity of medical liquid drawn into the syringe 1 is obtained from the position to which the piston 3 is moved which is measured using a scale M provided on the outer periphery of the syringe 1.

A liquid introducing set 7 for connecting the syringe 1 to the body (blood vessel or bladder) has a liquid introducing tube 7a, a terminal 7b provided at one end of the liquid introducing tube 7a that can be connected to the base 2 of the syringe 1 with a second connection piece 8 therebetween, and a distal member 7c provided at the other end of the liquid introducing tube 7a that can be connected a needle or cannula (not shown) to be inserted into the blood vessel of the body or the like. The distal member 7c has in it a flow rate control tube (not shown) having a given inner diameter.

Figure 4:
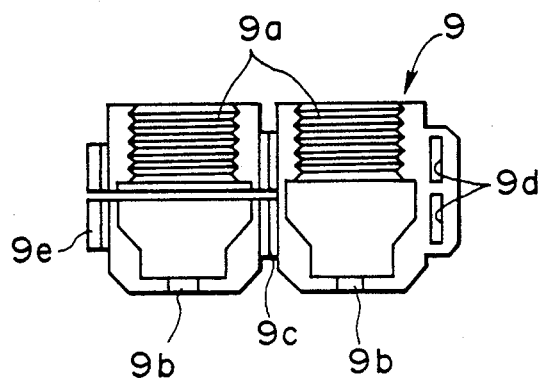
FIG. 4 is an exploded view of a chuck.

A chuck 9 encloses and thereby fixes the connecting portion of the base 2 of the syringe 1, the second connection piece 8 and the terminal 7b of the liquid introducing set 7. The chuck 9 prevents separation of the connecting portion due to the pressure of the medical liquid contained in the syringe which would occur when the medical liquid in the syringe is injected into the body. Provision of the chuck 9 is eliminated when locking of the connecting portion is possible. The chuck 9 has on the inner surface of the proximal end thereof a female screw (annular rib) 9a that can be engaged with the male screw (annular rib) 2b formed on the outer surface of the base 2 of the syringe 1, as shown in FIG. 4. The chuck 9 also has at the distal end wall thereof a hole 9b through which the liquid introducing tube 7a can pass. Normally, the chuck 9 is in an extended state, which is achieved by unhinging a hinge portion 9c. During the use, female piece 9d is coupled to a male piece 9e.

A germ removing filter (not shown) may be incorporated in the second connection piece 8.

Figure 2:
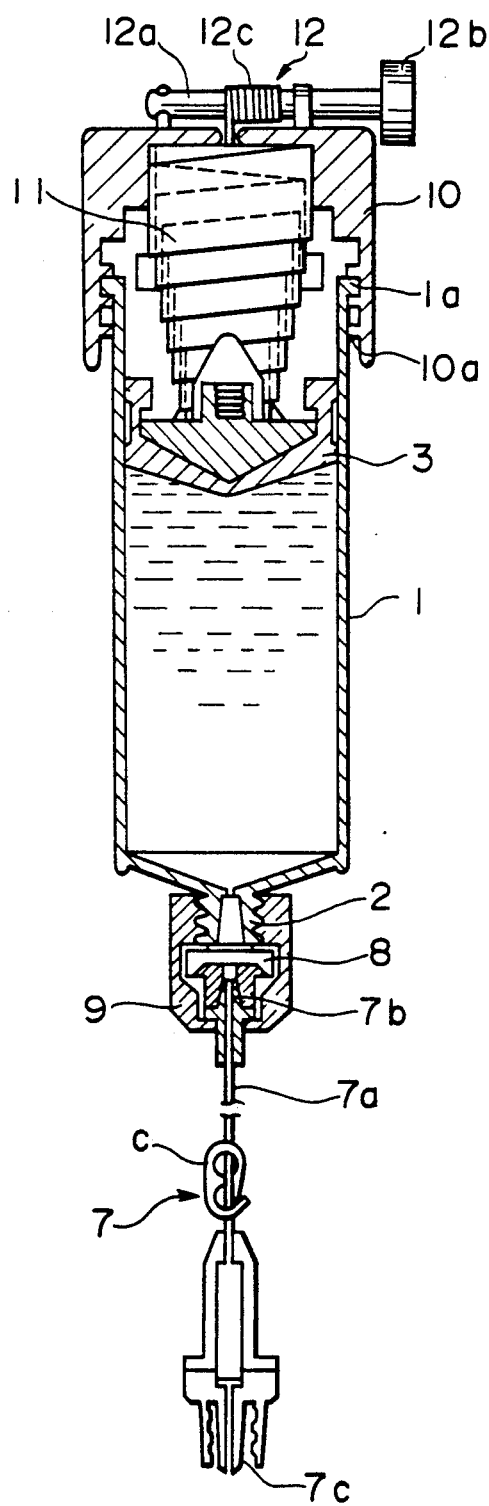
FIG. 2 is a plan view showing the state in which the medical liquid drawn in the syringe is going to be injected into a body.
Figure 3:
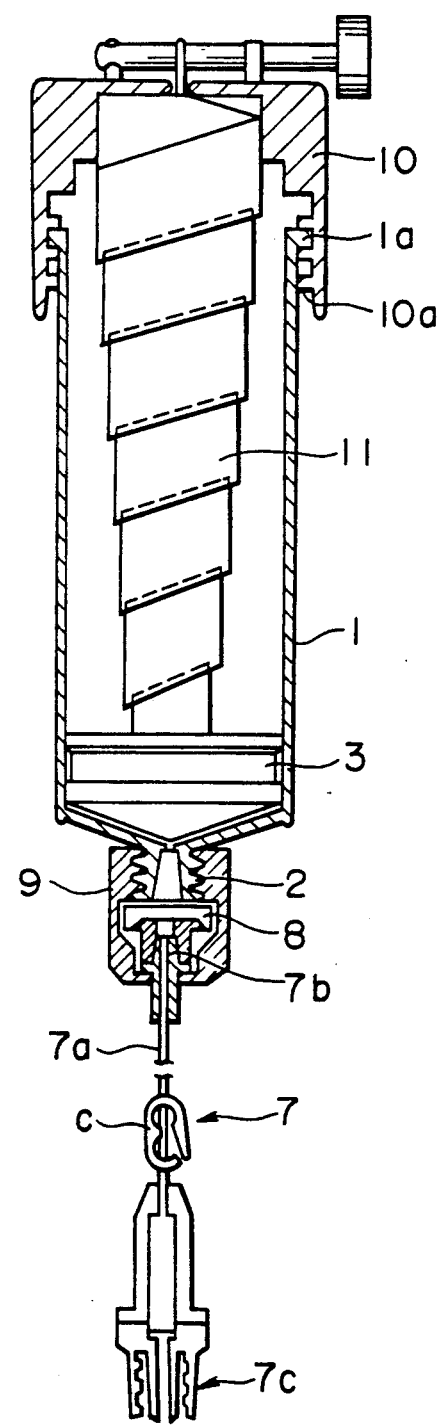
FIG. 3 is a plan view showing the state in which a piston has been pressed to a position where all of the medical liquid is pushed out.
Figure 5:
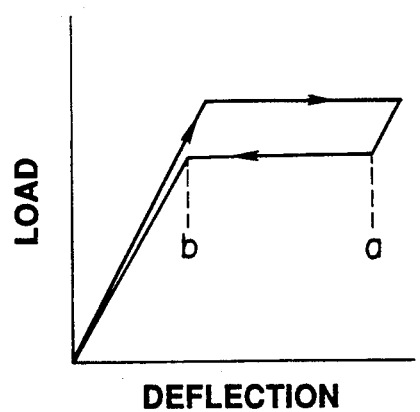
FIG. 5 is a graph showing the super resiliency of a bamboo shoot-like spring made of a shape memory alloy.

A cap 10 has a female screw 10a that can be engaged with an annular rib 9a provided on the outer periphery of the proximal end of the syringe 1. As shown in FIG. 2, the cap 10 has an elastic pressing means 11 for pressing the piston 3 located at the position in the syringe 1 where the medical liquid has been drawn in. The elastic pressing means 11 must be able to make contact with the rear surface of the piston 3 from which the shaft rod 4 is removed after the medical liquid has been drawn into the syringe 1 and to continuously press the piston 3 to the position where all the amount of medical liquid is pushed out, as shown in FIG. 3. To fulfill these requirements, the present embodiment employs a bamboo shoot-like spring made of a shape memory alloy exhibiting super elasticity, as shown in FIG. 5. However, any other means can also be used in place of the bamboo shoot-like spring. The bamboo shoot-like spring used in this embodiment is designed to continuously press the piston 3 from the maximum drawing position to the full amount pushing out position while it is deformed from the contracted state to the extended state in a super elastic area defined by 'a' point to 'b' point. A plurality of types of caps 10 may be prepared in terms of the type of elastic pressing force of the elastically pressing means 11 incorporated in the cap 10. An adequate elastic pressing means 11 may be selected with the relation between the medical liquid set 7 and the elastic pressing means 11 taken into consideration.

A deformation means 12 deforms the bamboo shoot-like spring, which forms the elastic pressing means and which is provided at the top of the cap 10, from the extended state to the contracting state. The deformation means 12 has a shaft 12a which is supported at two points on the outer surface of the cap 10, a knob 12b provided at one end of the shaft 12a, and a wire 12c which can be wound around the rotating shaft 12a which is rotated through the knob 12b so as to cause the bamboo shoot-like spring to contract. The knob 12b has a stopper (not shown) for fixing the wire at the wound position. The deformation means 12 may be omitted so that the spring can manually be caused to contract. Alternatively, any other means may be used in place of the aforementioned deformation means.

In this embodiment, a medical liquid is sucked into the syringe 1 first. To accomplish this, the needle 5 is connected to the base 2 of the syringe 1 through the first connection piece 6, and the piston 3 is pressed to one end of the syringe 1 by means of the shaft rod 4 mounted on the piston 3. Thereafter, the needle 5 is placed inside a medical liquid bottle and then the piston 3 is pulled slowly. An appropriate amount of medical liquid that is sucked into the syringe 1 can be confirmed from the position of the piston on the scale on the syringe 1.

Next, the shaft rod 4 is removed from the piston 3. Also, the combination of the first connection piece 6 and the needle 5 is separated from the base 2, and then the terminal 7b of the liquid introducing set 7 is connected to the base 2 through the second connection piece 8 and the connecting portion is enclosed and fixed with the chuck 9. Thereafter, a needle or cannula (not shown) is connected to the distal member 7c of the liquid introducing set 7. At that time, the midpoint of the liquid introducing tube 7a of the liquid introducing set 7 is clamped by a clamping tool C.

Subsequently, the cap 10 is capped to the proximal end of the syringe 1. Prior to the coupling, the shaft 12a of the deformation means 12 is rotated through the knob 12b so as to wind the wire 12c around the shaft 12a. The elastic pressing means (bamboo shoot-like spring) 11 is fixed in a contracting state with the stopper. After capping of the cap 10, fixing of the elastic pressing means 11 is released by removing the stopper. This causes the pressing means 11 to extend, and the extending elastic pressing means 11 presses against the rear surface of the piston 3. When this state has been attained, clamping of the liquid introducing tube is released so as to fill the medical liquid to the distal end of the needle or cannula. Thereafter, the needle or cannula is inserted into the body, by means of which the medical liquid in the syringe 1 is injected into the body little by little. The elastic pressing means 1 used in this embodiment is of the type which utilizes the super elastic area of the shape memory alloy spring. Pressing of the piston 3 is conducted until the piston 3 reaches the position where all the quantity of medical liquid is pushed out at a fixed force. Furthermore, all the quantity of medical liquid is pushed out by the time the piston reaches the position where all the quantity of medical liquid is pushed out.

Figure 6:
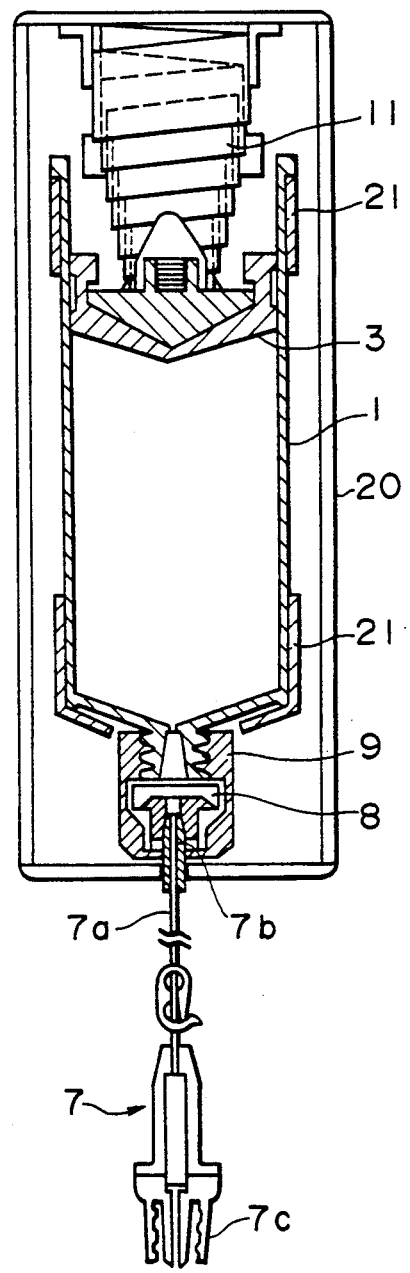
FIG. 6 is a plan view showing a second embodiment of the present invention.
Figure 7:
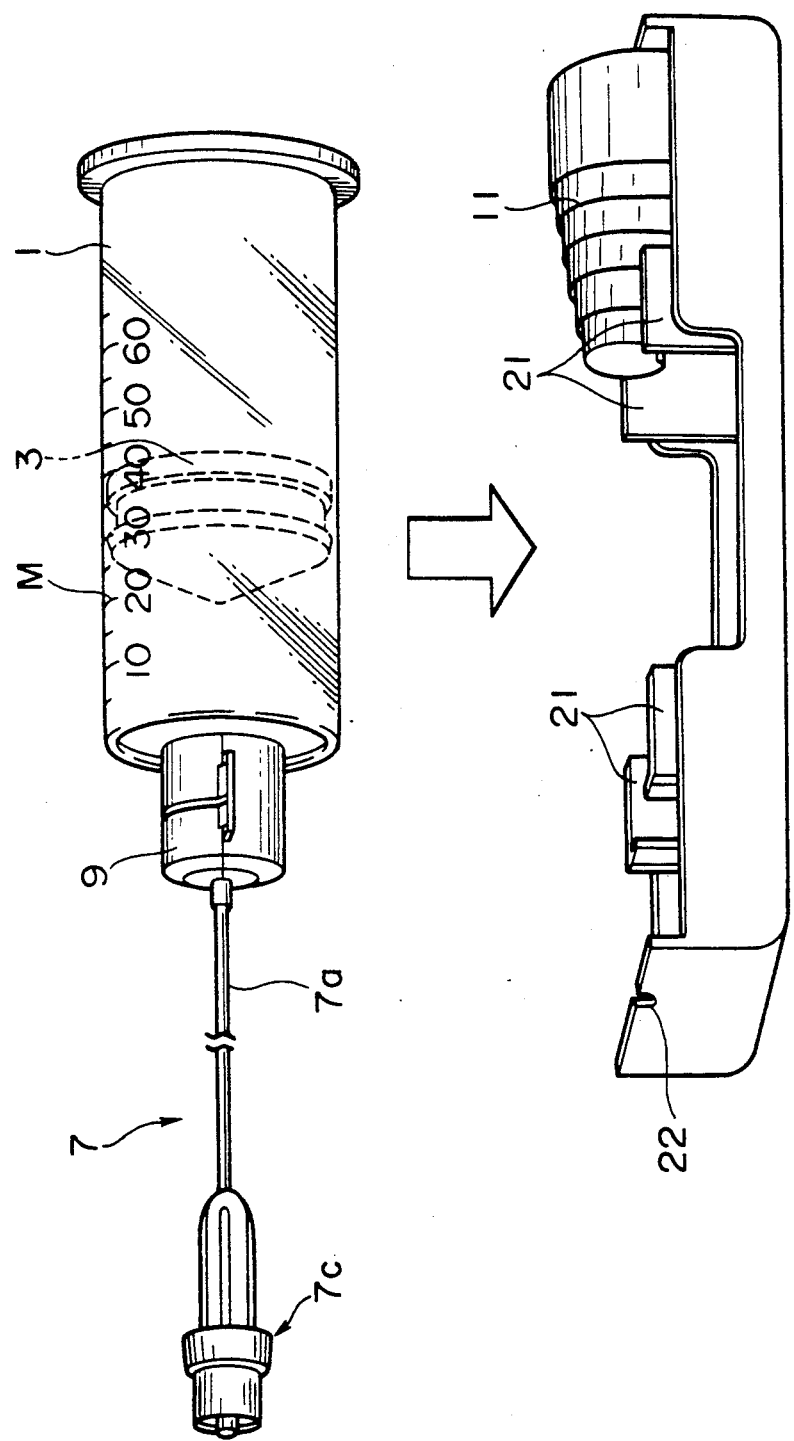
FIG. 7 is a perspective view of a syringe and a casing.

A second embodiment of the present invention will be described with FIGS. 6 and 7. A casing 20 for fixing the syringe 1 has a syringe retaining frame 21 at the bottom surface thereof. The casing 20 has a groove 22 through which the liquid introducing tube 7a of the liquid introducing set 7 connected to the base 2 of the syringe 1 can pass.

The elastic pressing means 11 for continuously pressing the piston 3 of the syringe 1 fixed within the casing 20 to the position where all the quantity of medical liquid is pushed out is provided on the side wall of the casing 20 which opposes the proximal end portion of the syringe 1. In this embodiment the elastic pressing means 11 may be made of the same material as that of the first embodiment. The compressing means of the elastic pressing means 11 may have the same structure as that of the first embodiment.

The syringe 1 may also have the same configuration as that of the first embodiment.

As will be understood from the foregoing description, the injector according to the present invention includes a syringe fitted with a piston having a detachable shaft rod, and a cap that can be coupled to the proximal end portion of the syringe. The inner surface of the cap is provided with the elastic pressing means for continuously pressing the piston from which the shaft rod is removed after the medical liquid is sucked into the syringe to a position where all the amount of medical liquid is pushed out. Consequently, the injector according to the present invention has advantages in that it can be carried from one place to another easily, that it is capable of continuously injecting the medical liquid contained in the syringe into the body at a fixed rate, and that it is capable of injecting all the amount of medical liquid contained in the syringe into the body to the last drop.

The elastic pressing means for continuously pressing the piston may be provided in a casing for fixing the syringe.

Furthermore, the use of the elastic pressing means which utilizes the super elastic area of a shape memory alloy further improves the fixing property of the amount of medical liquid injected.

What is claimed is:

1. A medical liquid injector for continuous transfusion, comprising:
   a syringe having a piston with a detachable shaft rod, said shaft rod being removed after a medical liquid is drawn into said syringe;
   a casing for fixing said syringe; and
   a resilient pressing means set on a side wall of said casing facing a proximal end of the syringe, after said shaft rod is removed, which after said medical liquid has been sucked into said syringe, is capable of continuously pressing said piston from which said shaft rod has been detached, up to a position where a full amount of the medical liquid is pushed out,
   said resilient pressing means comprising a shape memory alloy spring wound as a bamboo-shoot-like spring so that said shape memory alloy spring resiliently presses the piston from a maximum drawing position to a full amount pushing out position in a super elastic area of said shape memory alloy spring therein to press the piston at a constant force.

* * * * *